United States Patent [19]

Bellemin et al.

[11] Patent Number: 5,141,735
[45] Date of Patent: Aug. 25, 1992

[54] SUBSTITUTED AMINO-BENZODIAZEPINES HAVING ANITVIRAL ACTIVITY

[75] Inventors: Anne R. Bellemin, North Brunswick; James V. Earley, Cedar Grove, both of N.J.; Ming-Chu Hsu, New York, N.Y.; Steve Yik-Kai Tam, West Caldwell, N.J.

[73] Assignee: Hoffman-La Roche, Inc., Nutley, N.J.

[21] Appl. No.: 539,500

[22] Filed: Jun. 18, 1990

[51] Int. Cl.$^5$ .................. C07D 243/14; A61K 31/55
[52] U.S. Cl. .................................. 424/85.1; 424/85.2; 424/85.4; 424/85.5; 424/85.6; 424/85.7; 514/221; 514/46; 514/49; 514/50; 540/570; 540/571
[58] Field of Search .................. 540/571; 514/221, 8, 514/12, 49, 50, 44, 46; 424/85.1, 85.2, 85.4, 85.6, 85.7

[56] References Cited

U.S. PATENT DOCUMENTS

| | | | |
|---|---|---|---|
| 3,100,770 | 8/1963 | Fryer et al. | 260/239.3 |
| 3,267,110 | 8/1966 | Pachter et al. | 260/296 |
| 3,330,481 | 1/1967 | Bell et al. | 260/239.3 |
| 3,398,159 | 8/1968 | Berger et al. | 260/326.5 |
| 3,400,128 | 9/1968 | Berger et al. | 260/256.4 |
| 3,405,122 | 10/1968 | Berger et al. | 540/571 |
| 3,407,211 | 10/1968 | Berger et al. | 260/326.3 |
| 3,692,777 | 9/1972 | Arima | 260/239.3 |
| 3,778,433 | 12/1973 | Yamamoto et al. | 260/239.3 |
| 3,794,644 | 2/1974 | Karlyone | 260/239.3 |
| 3,954,728 | 5/1976 | Sternbach et al. | 260/296 |
| 4,788,181 | 11/1988 | Driscoll et al. | 536/23 |
| 4,939,177 | 7/1990 | Miller | 514/729 |

FOREIGN PATENT DOCUMENTS 0336466 10/1989 European Pat. Off. .

OTHER PUBLICATIONS

Sandström et al., Review Article in *Drugs*, 34, pp. 373-390 (1987).
Yarchoan et al., *AIDS Modern Concepts and Therapeutic Challenges*, Marcel Dekker, Inc., New York, pp. 335-360 (1987).
CA88(13): 89725c (Japan Kokai JP 77/83,891), 1977.
Pauwels, et al., Nature 343: 470-474 (Feb. 1990).
J. Chem. Res., Synop. (12) 399 (1980), Clarke et al.

*Primary Examiner*—Mukund J. Shah
*Assistant Examiner*—Philip L. Datlow
*Attorney, Agent, or Firm*—George M. Gould; William H. Epstein; Patricia S. Rocha

[57] ABSTRACT

Novel substituted 2-amino-5-(1H-pyrrol-2-yl)-3H-1,4-benzodiazepines and compositions containing same for treatment and prophylaxis of viral infections, including HIV infections.

13 Claims, 5 Drawing Sheets

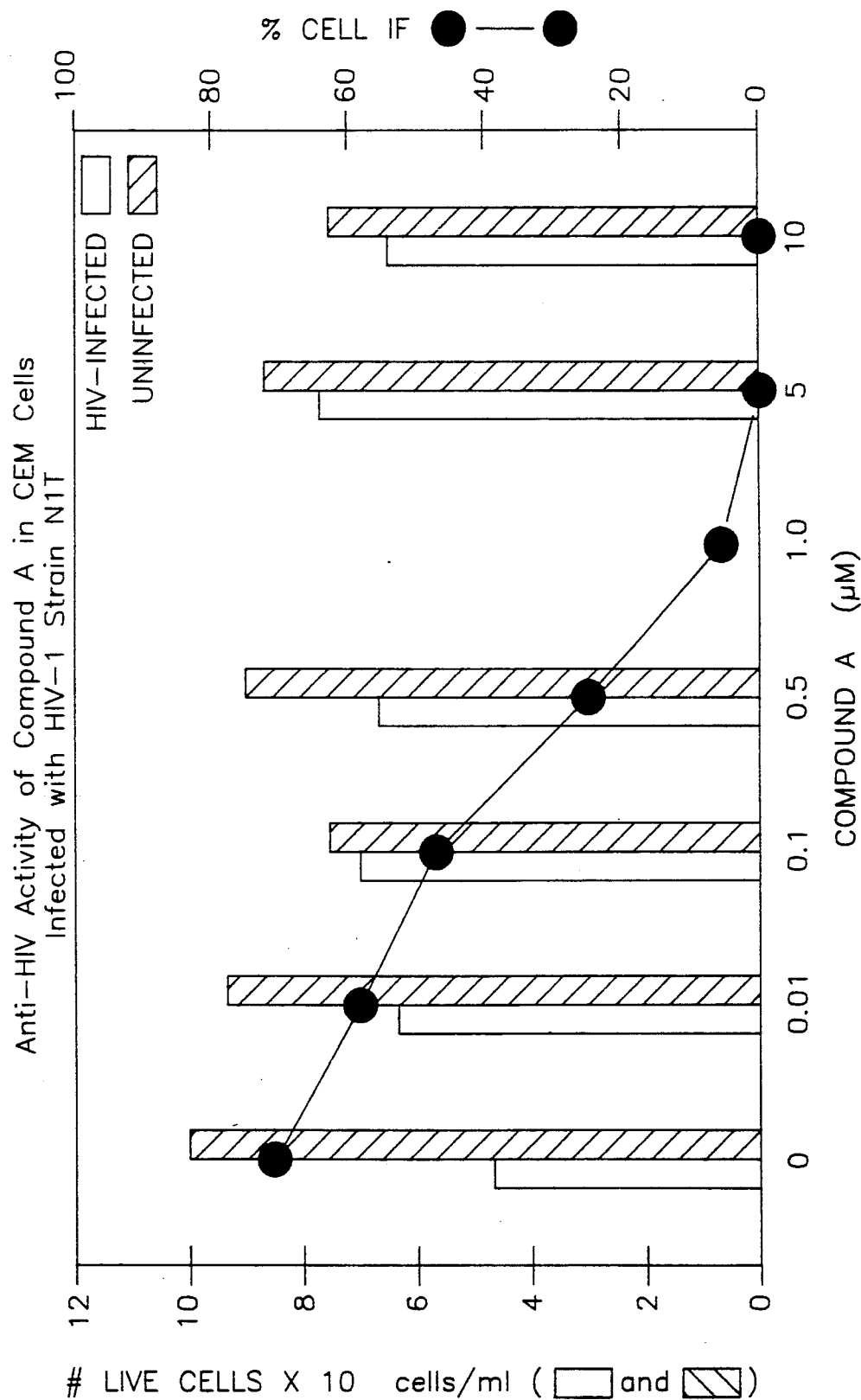

Anti-TAT Activity of Compound A Demonstrated With a Transfection-Based Assay

SUBSTITUTED AMINO-BENZODIAZEPINES HAVING ANITVIRAL ACTIVITY

FIELD OF THE INVENTION

The present invention relates to novel substituted 2-amino-5-(1H-pyrrol-2-yl)-3H-1,4-benzodiazepines. These novel compounds have useful antiviral activity, particularly activity against HIV, the virus implicated in the development of AIDS. These compounds also inhibit HIV replication by inhibiting such important HIV viral functions as transactivating transcriptional (TAT) activity.

BACKGROUND OF THE INVENTION

Human immunodeficiency virus type I and type II (HIV-1 and HIV-2, hereinafter referred to collectively as "HIV") are recently discovered retroviruses. HIV exerts a profound cytopathic effect on the CD4+ helper/inducer T-cells, devastating the function of the immune system, and also causes neurological deterioration. The virus is the etiologic agent of the acquired immune deficiency syndrome (AIDS) and related diseases such as AIDS Related Complex (ARC).

AIDS is an ailment of worldwide concern. The World Health Organization estimates that by 1992, the number of AIDS cases will be about 1.2 million.

The field of viral chemotherapeutics has developed in response to the need for agents effective against retroviruses, particularly HIV. There are many ways in which an agent can exhibit antiretroviral activity, one of which is through inhibition of viral replication. For example, the HIV virus requires at least four viral proteins for replication: Reverse Transcriptase (RT), protease, the transactivator protein TAT, and the REV protein. Anti-retroviral agents such as AZT or ddC are known to be RT inhibitors. Other agents such as TAT inhibitors act at a different stage of the viral life cycle.

HIV replication in latently infected CD4+ lymphocytes is induced when the cells are stimulated to proliferate by cytokines or mitogens. The switch from viral latency to active replication requires the regulatory gene products TAT and REV. The TAT protein transactivates the HIV-LTR promoter and amplifies viral replication many thousand fold. The TAT responsive sequence is mapped within the LTR sequence. Compounds which have anti-HIV-TAT activity will arrest HIV at the latent stage of viral infection by preventing transcription of the provirus that is integrated into the host cell chromosome. Anti-TAT agents are thus useful for therapeutically treating patients infected with HIV, including AIDS and ARC patients, and other symptomatic and asymptomatic carriers of the virus.

A summary of antiviral drugs being investigated for the treatment of AIDS, including AZT, is provided in U.S. Pat. No. 4,788,181. It is noteworthy, however, that the data on patients treated with AZT, the only compound now approved for AIDS therapy, indicates that AZT does not eliminate viremia in patients, and eventually the appearance of drug-resistant mutant viruses is evidenced. Consequently, there is still a great need for therapeutic agents for the treatment and alleviation of AIDS and AIDS related diseases and symptoms.

Certain 3H-1,4-benzodiazepine compounds containing a 5-membered heterocyclic ring as a substituent in the 5-position are taught in U.S. Pat. Nos. 3,405,122, 3,400,128, 3,398,159 and 3,407,211. In particular, formula IV, column 1, of each of these patents discloses the generic structure for several substituted amino-3H-1,4-benzodiazepine compounds. However, the specification provides no specific example of such substituted amino compound. Moreover, these compounds are disclosed to be useful as sedatives, convulsants, tranquilizers or muscle relaxants.

Unexpectedly, applicants have discovered that certain novel substituted 2-amino-3H-1,4-benzodiazepine compounds exhibit antiviral properties; in particular, they have anti-HIV and anti-HIV-TAT activity. These compounds are useful as antiviral agents, in particular in the treatment, therapy or prophylaxis of AIDS and AIDS-related diseases.

SUMMARY OF THE INVENTION

The Present invention provides novel substituted 2-amino-5-(1H-pyrrol-2-yl)-3H-1,4-benzodiazepines.
The compounds of the present invention have the following general formula:

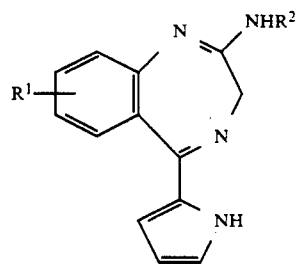

where $R^1$ is selected from H, $NO_2$, halogen, $CF_3$, lower alkyl, OH, O-alkyl, and cyano; and $R^2$ is selected from H and methyl.

This invention also includes the tautomers and pharmaceutically acceptable salts of compounds of formula I.

Compounds of formula I, alone or in combination with other antivirals and/or biological response modifiers, are effective in the treatment of virus infections, including retrovirus infections, e.g. AIDS, and other diseases caused by retroviruses. For example, these compounds were found to protect CD4+ lymphocytes in culture from the cytopathic effects of the HIV. These compounds also effectively inhibit the TAT proteins so that viruses being affected cannot replicate themselves in the host cells. Administration to an infected animal, including a human patient, may be oral, intravenous, or in another suitable manner. As used hereinafter, the term virus includes retroviruses.

The present invention also provides a method of treating a virus-infected cell or organism, including an HIV-infected cell or organism, comprising treatment with an effective amount of a substituted 2-amino-5-(1H-pyrrol-2-yl)-3H-1,4-benzodiazepine compound of the present invention or a biologically active metabolite thereof which reaches the interior of the cell or the target site in the organism.

The instant invention is also directed to a method for alleviating the cytopathic destructive effects of retroviral disease in a human patient infected with a retrovirus comprising administering to said patient an antiretrovirally-effective amount of a benzodiazepine according to this invention or a composition containing such a compound.

The instant invention also includes antiviral compositions comprising a therapeutically-effective amount of a compound according to the invention in a pharmaceutically-acceptable carrier.

In addition, because the use of more than one active agent may provide a better therapeutic composition, and this is particularly true when the different agents act by different mechanisms, this invention also includes antiviral compositions comprising both a compound according to the present invention together with one or more other antiviral agents, such as AZT, as well as biological response modifiers, including, for example, interferon (α, β or γ), interleukin-2 and granulocyte-macrophage colony stimulating factor ("GM-CSF") and the like.

For purposes of this invention, the terms "antivirally-effective" and "antiretrovirally effective" amount means an amount of a compound according to the invention that results in treatment, prophylaxis, slowing of spread of disease or of manifestations of disease, prevention of infection of others and/or improvement in patient condition.

BRIEF DESCRIPTION OF THE FIGURES

FIG. 1 shows the anti-HIV effect on HIV-1-infected CEM-cells (strain N1T) of a compound of formula I wherein $R^1$ is -Cl at position 7, and $R^2$ is —$CH_3$ [7-chloro-N-methyl-5-(1H-pyrrol-2-yl)-3H-1,4-benzodiazepin-2-amine, hereinafter "Compound A"]. As can be seen from FIG. 1, treatment with increasing concentrations of the claimed compound, represented by the X-axis, results in greater survival of HIV-infected cells, represented by the left-hand Y-axis (bars). Significantly, at concentrations of 5 μM of the test compound, the survival rate for the HIV-infected cells was very close to that of uninfected cells. In addition, the right-hand Y axis provides the percent of cells stained with antibodies from patient sera and visualized with fluorescein-conjugated goat anti-human IgG, a measure of HIV replication. The $ID_{50}$ and $ID_{90}$ are 0.5 μM and 1 μM, respectively.

FIGS. 2-1 and 2-2 show the anti-HIV activity in culture of Compound A (panel A) in acutely infected CEM cells in comparison to AZT (panel B) and ddC (panel C), which are known to have anti-HIV activity in infected patients. In this figure, the bars represent the number of live infected cells left Y-axis), as determined by trypan blue exclusion. The X-axis is the concentration of Compound A. The right-hand Y-axis provides two measurements:

is a measure of cell-associated viral RNA per $2 \times 10^5$ cells, is a measure of viral p24 antigen in culture media measured by ELISA (Abbott).

As can be seen from this figure, applicants' claimed compound results in at least similar, and at several compound concentrations, better, cell survival than AZT or ddC. Treatment with applicants' compound dramatically reduces the amount of cell-associated viral RNA and viral p24 antigen in the cells.

Figure 3:
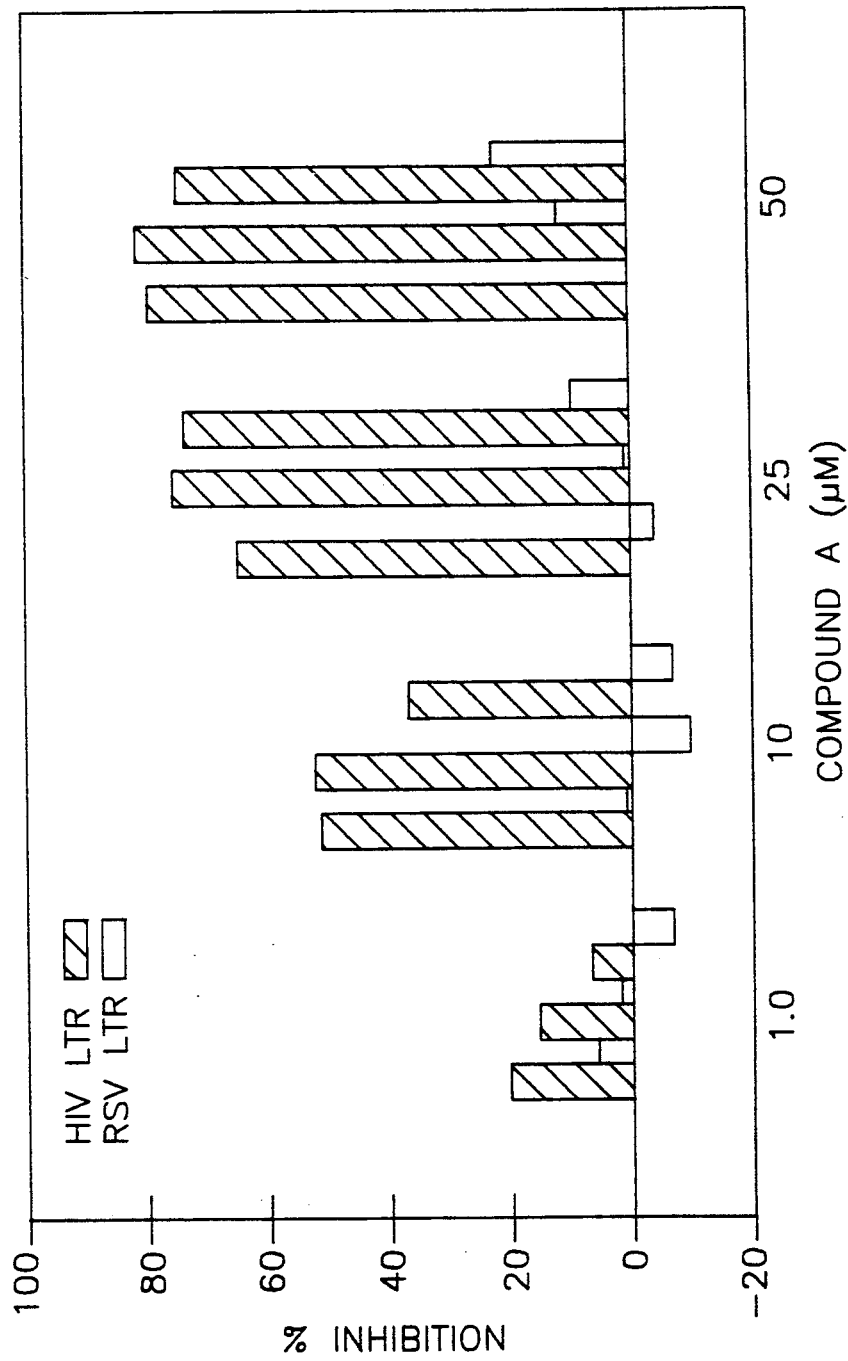

FIG. 3 shows the anti-TAT activity of Compound A with a transfection assay. The results of three assays are shown in this figure. The specificity of the inhibitory effect is demonstrated with the RSV LTR-driven SeAP gene expression which is not responsive to TAT.

Figure 4:
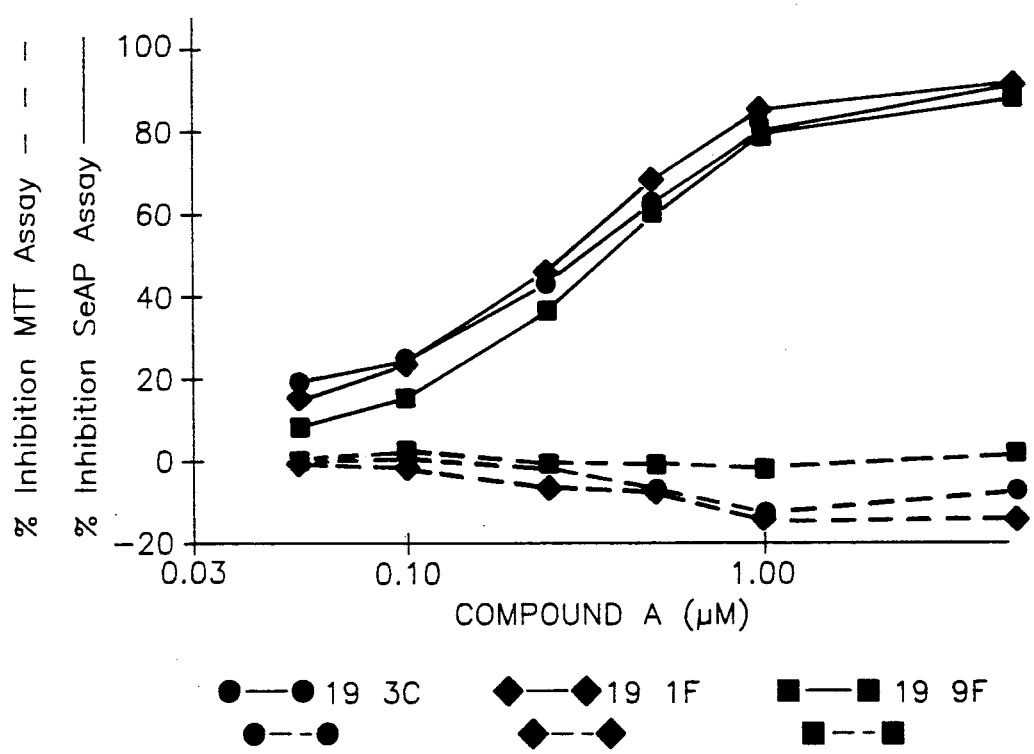

FIG. 4 shows the anti-TAT activity of Compound A in cell lines constitutively expressing SeAP. The Y-axis is (1) the percent inhibition in TAT transactivation measured according to SeAP activity in culture media (discussed infra), and (2) a measurement of cytotoxicity based on an MTT assay. The MTT assay is a known tetrazolium-based assay which measures the viability of cells. The X-axis is the concentration of compound. The solid circles, diamonds and squares represent the three different cell lines identified at the bottom of the Figure.

DETAILED DESCRIPTION OF THE INVENTION

The substituted 2-amino-5-(1H-pyrrol-2-yl)-3H-1,4-benzodiazepines of the present invention have the following general formula:

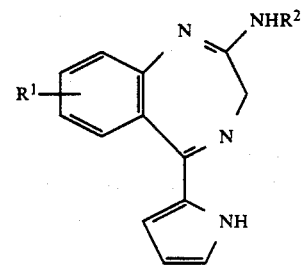

where
$R^1$ is selected from H, $NO_2$, halogen, $CF_3$, lower alkyl, OH, O-alkyl, and cyano; and
$R^2$ is selected from H and methyl.

As used in this specification, the following terms have the given meaning:

"Lower alkyl" refers to straight or branched carbon chains having from 1 to 7 carbon atoms such as methyl, ethyl, propyl, isopropyl, and the like.

It is understood that for compounds which can exist in stereoisomeric or tautomeric forms, all stereoisomeric and tautomeric forms are included in the scope of this invention.

Preferred compounds are those having the formula

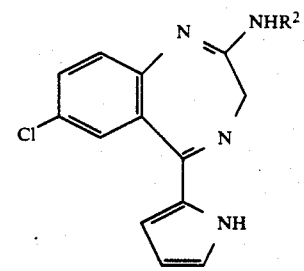

where $R^2$ is selected from H and methyl.

The compounds of formula I are synthesized by conversion of an amide compound of formula III following a variety of procedures known in the art. For example, a compound of formula III can be stirred with an amine of formula IV in an appropriate reaction-inert solvent in the presence of a suitable Lewis acid to yield a compound of formula I as shown below. See, for example, U.S. Pat. No. 3,644,335, which is hereby incorporated by reference. Examples of appropriate reaction-inert solvents include, but are not limited to, tetrahydrofuran, toluene and dioxane. Examples of suitable Lewis acids include, but are not limited to, titanium tetrachloride, stannic chloride and the like.

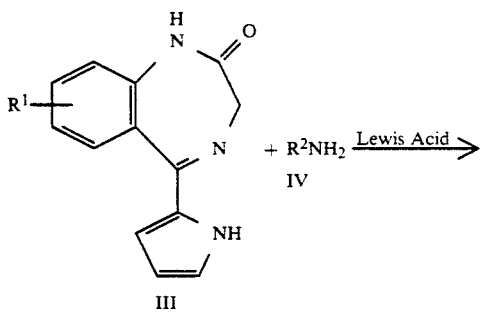 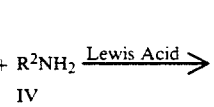 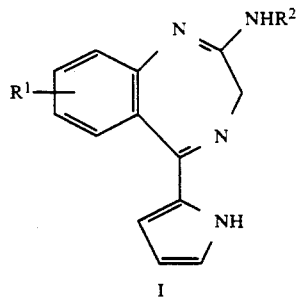

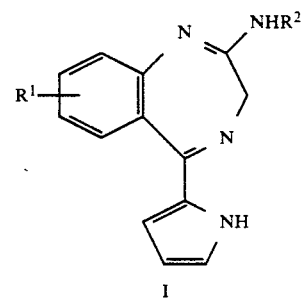

Compounds of formula III above are known and are synthesized according to methods disclosed in U.S. Pat. Nos. 3,405,122, 3,398,159, 3,407,211 and 3,400,128, all of which are hereby incorporated by reference.

Alternatively, compounds corresponding to formula I can also be prepared by a reaction of an intermediate of formula V below with an amine of formula IV. This procedure is known in the art, see for example, J. Org. Chem. (1964) 29, 231, herein incorporated by reference.

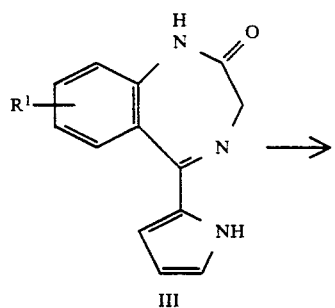

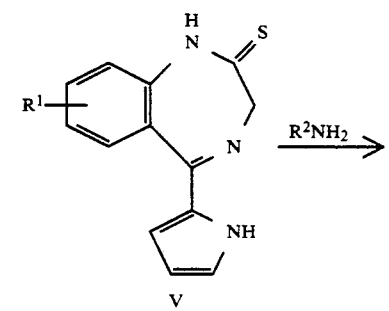

The intermediates of formula V can be obtained by stirring a compound of formula III with a thiation reagent, such as phosphorous pentasulfide, or Lawessen's reagent [2,4-bis(4-methoxyphenyl)-1,3-dithio-2,4-diphosphetane-2,4-disulfide], in an appropriate reaction-inert solvent, such as, for example, tetrahydrofuran, toluene, pyridine and dioxane. In order to increase the reaction rate, the reaction is usually carried out at elevated temperatures, e.g. between 50° and 100° C., or in an ultrasonic water bath.

The compounds of the present invention are antiviral agents which exhibit anti-HIV and anti-HIV-TAT activity as set forth in the following Examples, Tables and Figures.

This invention includes treatment or therapy of patients infected with HIV, including AIDS or ARC patients and patients with symptomatic or asymptomatic HIV infections. With respect to a human patient, an antivirally-effective amount of a compound of formula I is in the range of from about 0.1 to about 10 mg/kg body weight per day, preferably from about 0.3 to about 5 mg/kg, more preferably from about 1 to about 3 mg/kg body weight per day. This dosage may be administered parenterally or orally in one or more doses at various intervals daily, preferably orally once daily. It is understood that in patients with liver or kidney problems, dosing and forms of administration may have to be adjusted to accommodate these conditions.

With respect to human or other animal patients, the compounds of this invention may be administered in various dosage forms as set forth herein. Either the compounds, compositions, or their pharmaceutically acceptable salts are suitable. Pharmaceutically acceptable salts may be salts of organic acids such as lactic, acetic, malic, or p-toluenesulfonic acid and the like as well as salts of pharmaceutically acceptable mineral acids such as hydrochloric and sulfuric acids and the like.

The compounds are administered in the dosages as set forth herein until alleviation of viremia. The compounds may also be administered with other antiviral and/or biological response modifiers. For example, the compounds of formula I may be administered with known RT inhibitors such as ddC, AZT and ddI or other inhibitors which act against other HIV proteins such as protease, integrase and RNAasH, as well as with biological modifiers such as interferon, -alpha, -beta or -gamma, or a combination thereof, interleukin-2 and GM-CSF. The dosages of ddC and AZT used in AIDS or ARC human patients have been published. An in vitro virustatic range of ddC is generally between 0.05 μM to 1.0 μM. A range of about 0.005–0.25 mg/kg body weight is virustatic in most patients. The preliminary dose ranges for oral administration are somewhat broader, for example 0.001 to 0.25 mg/kg given in one or more doses at intervals of 2, 4, 6, 8, 12, etc., hours. Currently 0.01 mg/kg body weight ddC given every 8 hours is preferred. When given in combined therapy, the other anti-HIV compounds may be given at the same time as a compound of formula I or the dosing may be staggered as desired. The two (or more) drugs may also be combined in a composition. Doses of each drug may be less when used in combination than when they are used as a single agent.

The instant invention is also directed to compositions containing a therapeutically-effective amount of a compound of formula I in a pharmaceutically-acceptable carrier. It is possible for the compounds of the invention to be administered alone in solution. However, it is preferred that the active ingredients be administered in a pharmaceutical formulation. In the context of the instant invention, formulation means composition. These formulations comprise at least one active ingredient together with one or more pharmaceutically acceptable carrier and excipient and may optionally include other therapeutic agents, for example a protease inhibitor. As included within the scope of this invention, "acceptable" is defined as being compatible with other ingredients of the formulation and not injurious to the organism or host cell being treated. These carriers include those well known to practitioners in the art as suitable for oral, rectal, nasal, topical, buccal, sublingual, vaginal, or parenteral (including subcutaneous, intramuscular, intravenous, and intradermal) administration.

The compounds of this invention may be used in the manufacture of pharmaceuticals for the treatment or prophylaxis of viral infections. The compositions may be conveniently presented in unit dosage form and prepared by methods known in the pharmaceutical art. Such methods include the preparation of the active ingredient in a carrier which may contain additional medicinally active ingredients, for example, ddC, AZT, interferon, IL-2 or a protease inhibitor. The compositions of the invention suitable for oral administration may consist of liquid solutions such as an effective amount of the compound dissolved in diluents such as water, saline, or orange juice. Capsules, sachets or tablets, each containing a pre-determined amount of the active ingredient, as a solid or granules; as a solution or suspension in an aqueous liquid; in an oil-in-water emulsion or a water-in-oil liquid emulsion, for example, soft gelatin capsules. Tablet forms may include one or more of lactose, microcrystalline cellulose, colloidal silicon dioxide, croscarmellose sodium, magnesium stearate, stearic acid and other excipients, colorants, and pharmacologically compatible carriers.

Formulations suitable for topical administration include lozenges comprising the active ingredient in a flavor, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for vaginal administration may be presented as vaginal suppository, tampons, creams, gels, pastes, foams, or spray formulas containing in addition to the active ingredient such carriers as are known in the art to be appropriate.

Formulations suitable for parenteral administration include aqueous and non-aqueous, isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

To better illustrate their invention, applicants provide the following examples.

EXAMPLES

Unless otherwise specified, percentages given in the examples for solids mixtures, liquids in liquids, and solids in liquids are on a wt/wt, vol/vol and wt/vol basis, respectively.

EXAMPLE 1

Synthesis of
7-chloro-N-methyl-5-(1H-pyrrol-2-yl)-3H-1,4-benzodiazepin-2-amine

A solution of 0.5 g (1.92 mmol) of 7-chloro-1,3-dihydro-5-(1H-pyrrol-2-yl)-1,4-benzodiazepin -2-one in 25 ml of dry THF was cooled in a dry ice/acetone bath and methylamine was bubbled through the solution for 5 minutes. To this solution, 0.29 ml (2.63 mmol) of $TiCl_4$ was added dropwise with stirring and after 5 hours at room temperature an additional 0.2 ml (1.79 mmol) of $TiCl_4$ was added. After 18 hours a small piece of ice was added and the reaction was filtered, washed with THF and concentrated. Crystallization from $CH_2Cl_2$/methanol, and recrystallization from ethanol gave 0.25 g (48%) of 7-chloro-N-methyl-5-(1H-pyrrol-2-yl)-3H-1,4-benzodiazepin-2-amine as off-white prisms having the following characteristics: mp 251° C.; IR (KBr) 3215, 3060 cm$^{-1}$. Anal. Calcd. for $C_{14}H_{13}ClN_4$: C 61.65; H 4.80; N 20.54. Found: C 61.33; H 4.93; N 20.20.

EXAMPLE 2

Synthesis of
7-chloro-5-(1H-pyrrol-2-yl)-3H-1,4-benzodiazepin-2-amine 10 g (38.5 mmol) of 7-chloro-1,3-dihydro-5-(1H-pyrrol-2-yl)-1,4-benzodiazepin-2-one were dissolved in anhydrous THF (400 ml) in a 1 litre round-bottom 3-neck flask equipped with a mechanical stirrer. The flask was then placed in the water bath of an ultrasonic apparatus. To the stirred reaction solution was added $P_4S_{10}$ (10 g; 22.5 mmol) and the reaction mixture was irradiated with ultrasound. The temperature was maintained at about 40° C. throughout the reaction. After 2.5 hours, an additional portion of $P_4S_{10}$ (10 g; 22.5 mmol) was added to the mixture and the reaction was continued for an additional 2 hours. The heterogeneous mixture was cooled to ambient temperature and filtered. After washing the solid by-product with several portions of $CH_2CL_2$, the filtrates were combined and approximately 80% of the solvent was removed in vacuo. The residual solution was basified with saturated sodium bicarbonate solution until a pH of about 8 was reached. The product which precipitated out was filtered. The filtrate was then extracted with $CH_2Cl_2$, followed by concentration in vacuo. The solids were combined and recrystallized in THF/Petroleum ether to give 9.9 g (94% yield) of 7-chloro-1,3-dihydro-5-(1H-pyrrol-2yl)-1,4-benzodiazepin-2-thione as a pale yellow powder having the following characteristics: m.p. 258°-260° C. dec.; IR (KBr) 3450, 3165 $cm^{-1}$. Anal. Calcd. for $C_{13}H_{10}ClN_3S$: C 56.62; H 3.66; N 15.24. Found: C 56.50; H 3.59; N 15.12.

Next, 0.5 g (1.83 mmol) of this powder was dissolved in a minimum volume of THF (5 ml) and the solution was diluted with 200 ml of methanol. The flask was then cooled to $-78°$ C. and ammonia was bubbled through the solution for 10 minutes. The reaction was then allowed to warm up to room temperature and stirred for another 12 hours. The solvent was evaporated and 7-chloro-5-(1H-pyrrol-2-yl)-3H-1,4-benzodiazepin-2-amine was obtained as a yellowish gel (40% yield), having the following characteristics: m.p. 177°-179° C. dec; IR (KBr) 1638, 1590 $cm^{-1}$.

7-Chloro-1,3-dihydro-5-(1H-pyrrol-2yl)-1,4-benzodiazepin-2-thione is thus a useful intermediate in the synthesis of compounds of formula I.

The above-synthesized compounds were tested for anti-HIV and anti-HIV-TAT as described in Examples 3 and 4 below.

EXAMPLE 3

Testing of Compounds for Inhibition of HIV-Cytopathic Effect and Inhibition of Viral RNA and Antigen Production Compounds were tested directly for their anti-HIV effect. The assay protocols for the inhibition of HIV-cytopathic effect and the reduction of cell-associated viral antigens were modified from published procedures (Mitsuya, et al. P.N.A.S., USA 83:1911 (1986), and Hedenskog et al., J. Med. Virol. 19:325 (1986)).

High titer virus stocks (HIV-1 NIT strain or HIV-2 uc-1 strain) were grown in CD4+CR10 cells in RMPI-1640 media (Gibco Laboratories) supplemented with 10% fetal calf serum and 0.1 mg/ml Gentamicin. The collected media were filtered through a 0.8 micron filter and virus isolates were concentrated 100 fold and stored at $-80°$ C.

CD4+CEM cells, propagated in the same medium, were incubated for 60 minutes at 37° C. with diluted stock virus at a multiplicity of infection equal to 1 ( MOI=1, approximately 1 pg p24 or 4,000 viral particles per cell). Cells were washed three times with phosphate buffered saline and resuspended in the medium at $2\times10^5$ cells/ml. Various quantities of the test compound in DMSO, synthesized as described above were added. Four days after infection, the number of live cells were counted by trypan blue exclusion (Mitsuya, et al. Proc. Natl. Acad. Sci. 83:1911 (1986)). At the same time, aliquots of cells were fixed with acetone and stained with antibodies from AIDS patients, followed by a second staining with fluorescein-conjugated goat anti-human IgG (Cappel). Cells stained with the fluorescent antibody were counted using a fluorescence microscope and the results were expressed as percentage of the total number of cells counted (Hedenskog et al., J. Med. Virol 19:325 (1986)).

The results are shown in Table I below.

TABLE I

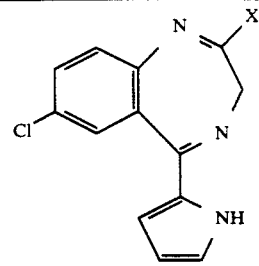

| X | Anti-HIV* $ID_{50}$ ($\mu M$) |
|---|---|
| $NH_2$ | 1 |
| $NHCH_3$ | 0.5-1 |
| | (Compound A) |

*$ID_{50}$ ($\mu M$) is the concentration of test compound that reduces the number of immunofluorescence positive cells by 50%.

As an additional measure of anti-HIV activity, the amount of p24 antigen in the culture media was measured by ELISA (Abbott) according to the procedure described by the manufacturer. This measurement is an indication of HIV virus replication.

In addition, the viral RNA in infected cells was quantified with an RNA-RNA hybridization/reversible target capture procedure [Gillespie et al. Molecular and Cellular Probes, 2:73 (1989)]. Reagents were purchased from GeneTrack System (MA, USA) and assays were carried out according to the procedure described by the manufacturers. $2\times10^5$ live cells, determined by trypan blue exclusion, were used in each assay.

For cytotoxicity testing, CEM cells were treated with a compound formula I at similar concentrations and the toxicity of the compound was measured by the live-cell count.

Figures 1, 2:
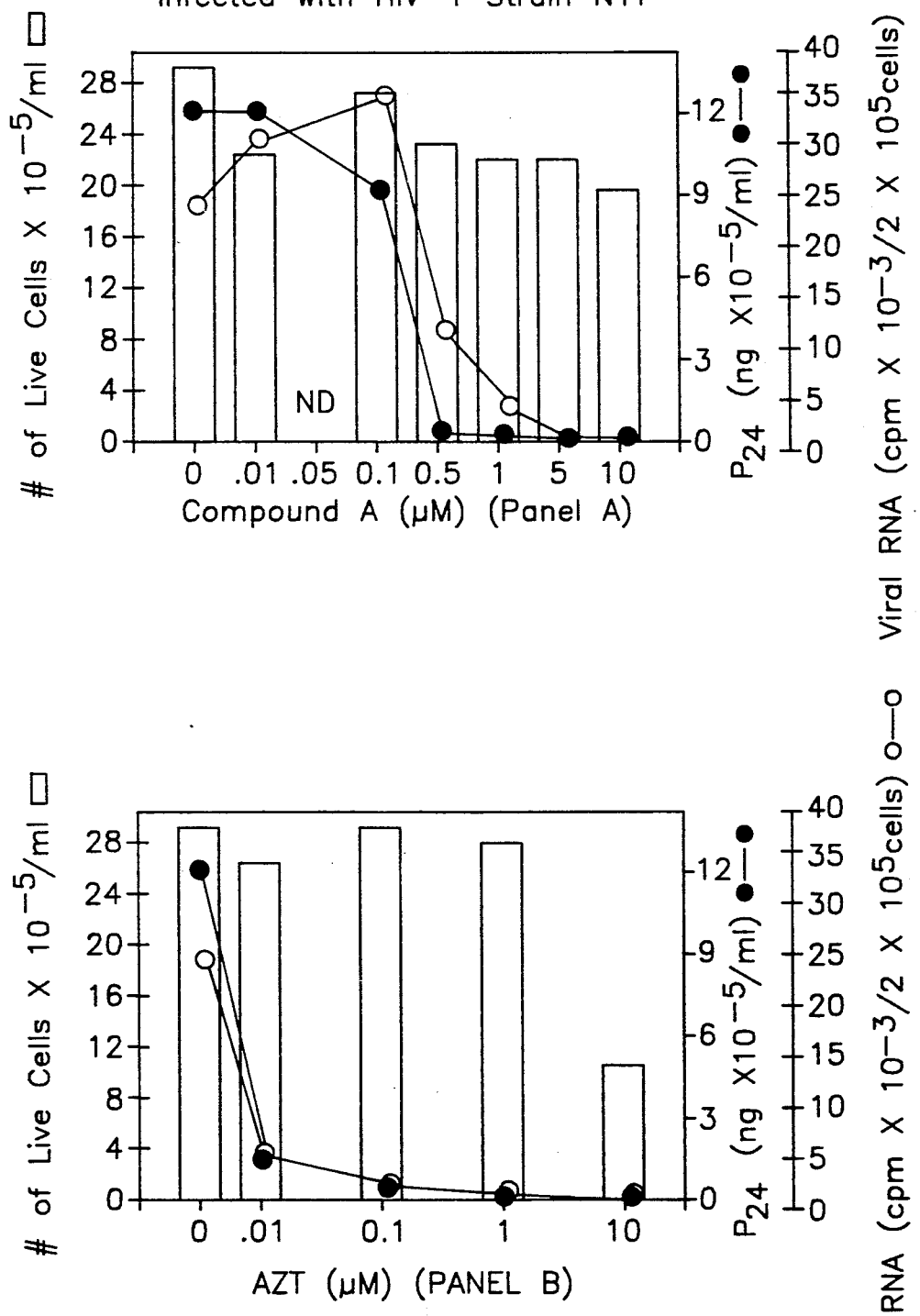
Figure 2:
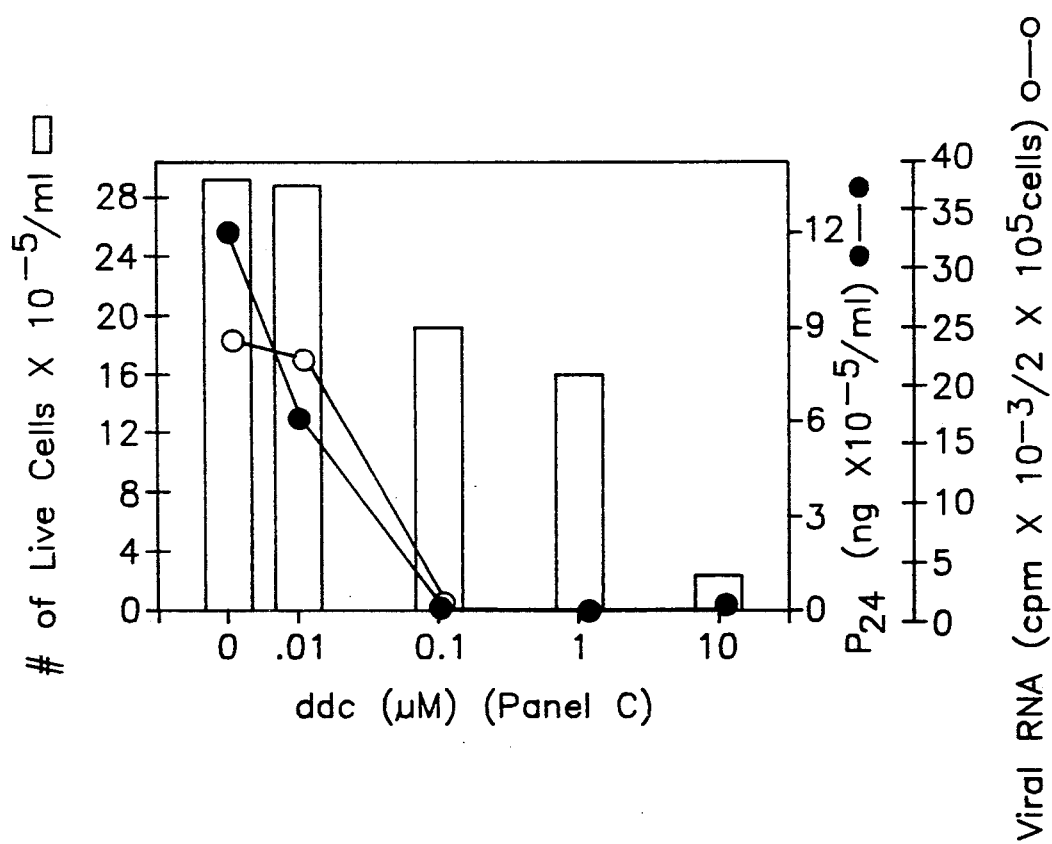

FIGS. 1 and 2 depict the anti-HIV activity of applicants' Compound A. FIG. 1 shows the survival rate of HIV-1-infected CEM-cells treated with Compound A. FIG. 1 also shows that treatment of cells with increasing amounts of Compound A results in the decline in the percentage of cells that are immunofluorescence-positive following staining with HIV antibodies. FIG. 2 provides a comparison of anti-HIV activity, as measured by cell survival and p24 antigen and viral RNA amount of applicants' Compound A versus AZT and ddC.

EXAMPLE 4

Measurement of Anti-HIV-TAT Activity

1. Transfection Assay

The compounds of the present invention were also tested for anti-HIV-TAT activity in an anti-TAT assay described in co-pending patent application U.S. Ser. No. 07/428,555, filed on Oct. 30, 1989, and hereby incorporated by reference. This assay comprises the following steps:

(a) putting both the expression of the Secreted Alkaline Phosphatase (SeAP) gene and the viral transactivator TAT gene under the control of the HIV promoter LTR responsive to the action of the HIV transactivator TAT;

(b) transfecting cultured mammalian cells with plasmids which contain the gene constructs of (a) above and cause cellular production of the transactivating factor TAT and SeAP;

(c) adding the agent to be tested, here compounds of formula I; and (d) determining the amount of SeAP produced by measuring SeAP enzymatic activity, whereby inhibition of SeAP production correlates with the anti-TAT inhibition activity.

In this assay, the inhibition of SeAP positively correlates with anti-TAT activity. The greater the ability of an agent to inhibit SeAP, the greater is its anti-TAT activity.

Specifically, with respect to the results reported below, the anti-HIV-TAT assay was run as follows:

At 24 hours post transfection 1, 10, 25 and 50 μM of a test compound of formula I was added to the culture media of COS cells transfected with two plasmids, one containing the reporter gene which codes for Secreted Placental Alkaline Phosphatase (SeAP) under control of HIV-LTR, and the other containing the HIV-TAT gene also under control of HIV-LTR. The alkaline phosphatase activity of the media was assayed 48 hours after addition of test compound with a colorimetric assay using p-nitrophenylphosphate as the substrate. The results of the anti-TAT assay for each compound tested are summarized in Table II. The amount provided in Table II for each compound is the average of three independent assays of each test compound.

The specificity of compounds of formula I as TAT inhibitors was demonstrated with a parallel assay in which the SeAP gene expression is controlled by the Rous sarcoma virus (RSV)-LTR which does not respond to TAT. This assay thus eliminates the possibility that compounds of formula I are either general cytotoxic agents or inhibit the activity of SeAP.

The anti-TAT activity reported in Table II is a comparison of the percent inhibition of SeAP gene expression under the control of HIV-LTR versus the percent inhibition of SeAP gene under RSV-LTR, which does not respond to TAT.

Table II below shows that compounds of formula I are specific inhibitors of HIV-TAT-regulated gene expression without non-specific cytotoxic effects.

TABLE II

[Structure: chlorophenyl compound with N-X substituent and NH-containing ring]

| X | Anti-HIV-TAT* Activity (% Inhibition) |
|---|---|
| NH₂ | >60 |
| NHCH₃ | >60 |

*Anti-HIV-TAT Activity
The anti-HIV-TAT activities of the compounds tested were determined by measuring the amount of alkaline phosphatase in the supernatant media of cultures of cells in which SeAP gene expression was under the control of the HIV LTR promoter. The specific inhibitory activities of the test compounds were calculated according to the formula:

$$\left[\left(1-\frac{A}{B}\right)-\left(1-\frac{C}{D}\right)\right]\times 100$$

where A and B are the alkaline phosphatase activities produced by HIV-LTR/SeAP in the presence and absence, respectively, of test compound, and C and D are the alkaline phosphatase activities produced by RSV-LTR/SeAP in the presence and absence, respectively, of test compound. The concentrations tested ranged from 1-50 μM. The results provided are the average of at least three tests. It is noted that each test compound was added 24 hours after cells were transfected with the plasmids when SeAP specific mRNA and protein were already present and the protein was very stable. Therefore, 100% inhibition would not be observed with this assay procedure. FIG. 3 reports the results of three repeat assays for Compound A.

2. Constitutive Cell Line Assay

Compounds of formula I were also tested for anti-HIV-TAT activity with cell lines that constitutively express the SeAP gene under the control of the HIV-LTR. Cell lines 193c, 191F and 199F were derived from CHO cells (cell line of Chinese hamster ovary origin). Each line is of clonal origin and has the HIV-LTR/SeAP and the HIV-LTR/TAT sequences integrated in the cellular chromosome. One day after cells were plated (approximately 30% confluency), a compound of formula I in DMSO (0.05% final concentration) was added to the culture media at desired concentrations. The cells were washed and Compound A was replenished one day later. SeAP activity was assayed two days after the second addition of test compound. The cytotoxic effect of the compound was measured with a MTT assay, an art-recognized measurement of cytotoxicity. See Denigot et al., J. Immunol. Methods 89:271 (1986). This assay also confirmed the specific anti-TAT activity of applicants' compounds. The results of this assay with Compound A are shown in FIG. 4.

FIG. 4 shows that while applicant's Compound A significantly inhibits SeAP expression under the control of the HIV-LTR promoter (demonstrated by the top set of lines), it has no cytotoxic effect on the cells (bottom set of dashed lines).

EXAMPLE 5

Formulations for Compounds of Formula I

| TABLET FORMULATION I | | |
|---|---|---|
| Item | Ingredients | Mg/Tablet |
| 1 | Active ingredient | 20 mg* |
| 2 | Starch | 40 mg |
| 3 | Avicel | 80 mg |
| 4 | Lactose | 274 mg |
| 5 | Magnesium Stearate | 2 mg |
| | | 416 mg |

Method for Preparation:
1. Mix Items 3 and 4 in a suitable blender.
2. Add and mix the active ingredient to the mixture from Step 1.
3. Add and mix Item 2 to the mixture from Step 2.
4. Add and mix Item 5 to the mixture from Step 3.
5. Compress the granulation on a suitable tablet press.

| TABLET FORMULATION II | | |
|---|---|---|
| Item | Ingredients | mg/Tablet |
| 1 | Active Ingredient | 20 mg* |
| 2 | Lactose | 180 mg |
| 3 | Pregelatinized Starch | 15 mg |

Method for Preparation:
1. Mix Items 1, 2, 3, and 4 and granulate with water.
2. Dry the granulation at 45-50° C.
3. Pass the granulation through a suitable mill.
4. Add Items 5 and 6; mix.
5. Compress the granulation on a suitable tablet press.

13
-continued

SOFT GELATIN CAPSULE FORMULATION

| Item | Ingredients | mg/Tablet |
| --- | --- | --- |
| 1 | Active ingredient | 20 mg* |
| 2 | Ethoxylated Fatty acids | 500 mg |
| 3 | PEG 4000 | 100 mg |
| 4 | Vegetable Oils q.s. to | 1.0 g |

Method for Preparation:
1. Add and mix active ingredient with Items 2 and 4.
2. Add Item 3 to the material from Step 1 and mix.
3. Add vegetable oil to the required amount.
4. Fill into a suitable capsule.

ORAL LIQUID FORMULATION

| Item | Ingredients | mg/Tablet |
| --- | --- | --- |
| 1 | Active ingredient | 20.0 mg* |
| 2 | Methylparaben | 20.0 mg** |
| 3 | Sucrose | q.s. |
| 4 | Flavoring Agent | q.s. |
| 5 | Citrate Buffer | q.s.*** |
| 6 | Purified Water q.s. | 5.0 mL |

Method for Preparation:
1. Dissolve Items 2, 4 and 5 into purified water.
2. Add active ingredient and dissolve into the solution from Step 1.
3. Add Item 3 and dissolve.
4. Add water to the required amount.
5. Fill the solution into a suitable container.

*The amount of active ingredient may be varied as required. The active ingredient may consist of a compound of formula I alone or in combination with another agent, such as another antiviral agent and/or a biological response modifier.
**For all of the above formulations, the amount of ddC may be varied as required.
***For all of the above formulations, solvents or solubilizers such as polyethylene glycols, alcohol, dimethylacetamide, glycerine, povidone, lecithin, sorbitan monooleate and trioleate, polysorbate 20 or 80 may be used in combination or alone to achieve the adequate solubility and stabilization.

Many modifications and variations of this invention may be made without departing from its spirit and scope, as will become apparent to those skilled in the art. The specific embodiments described herein are offered by way of example only, and the invention is to be limited only by the terms of the appended claims.

We claim:
1. A compound of formula

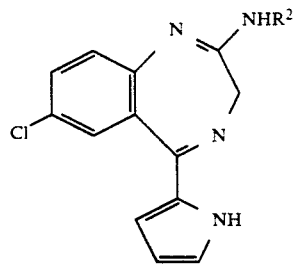

where $R^2$ is selected from the group consisting of H and methyl, and pharmaceutically acceptable salts thereof.

2. A compound of claim 1 having the formula

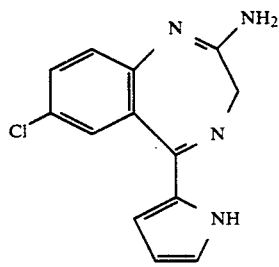

14

3. A compound of claim 1 having the formula

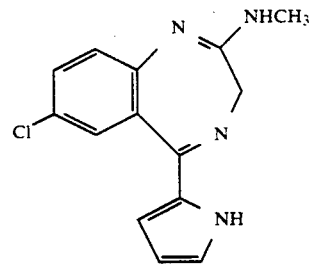

4. A method for treating a patient infected with a virus selected from the group consisting of HIV 1, HIV 2 or a combination of both, comprising administering to the patient a compound of formula II, claim 1, or a pharmaceutically acceptable salt thereof in an amount which is effective to treat said virus-infected patient.

5. The method of claim 4 wherein the antivirally-effective amount is from about 0.1 to about 10 mg/kg body weight per day in one or more doses.

6. The method of claim 5 wherein the antivirally effective amount is about 2 mg/kg body weight per day.

7. A method of protecting cells against a virus selected from the group consisting of HIV 1, HIV 2 and a combination of both, comprising treating said cells with an effective amount of a compound according to claim 1 or a biologically active metabolite thereof.

8. A method of protecting cells against HIV pathogenesis comprising treating said cells with an effective amount of a compound according to claim 1 or a biologically active metabolite thereof.

9. An antiviral composition comprising a therapeutically-effective amount of a compound of the formula II, claim 1, in a pharmaceutically-acceptable carrier.

10. The composition of claim 9 wherein the compound is

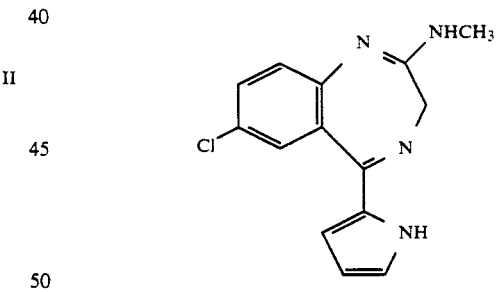

11. An antiviral composition comprising a therapeutically-effective amount of a compound having the formula:

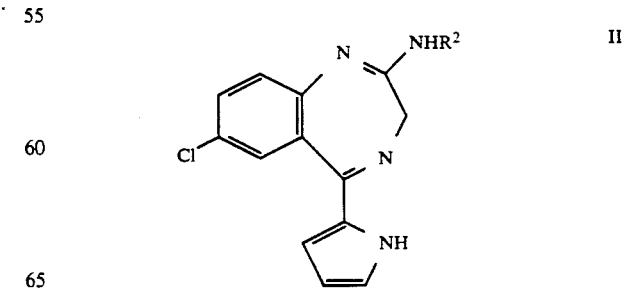

where $R_2$ is selected from the group consisting of H and methyl, in combination with a second antiviral agent.

12. The composition of claim 11 wherein the compound of formula II has the formula:

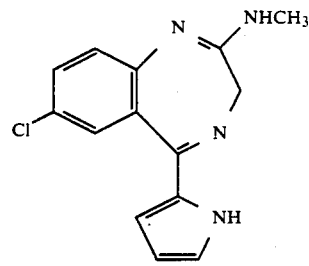

and the second antiviral agent is a reverse transcriptase inhibitor.

13. The composition of claim 11 wherein the second agent is selected from the group consisting of ddC, AZT, HIV-protease inhibitor, alpha-, beta- or gamma-interferon, or a combination thereof, interleukin-2- GM-CSF, and a combination thereof.

* * * * *